United States Patent [19]
Limousin et al.

[11] Patent Number: 5,645,576
[45] Date of Patent: Jul. 8, 1997

[54] METHOD AND APPARATUS FOR CONTROLLING THE BASE FREQUENCY OF A CARDIAC PACEMAKER

[75] Inventors: Marcel Limousin, Montrouge; Jean-Luc Bonnet, Vanves; Anne Bouhour, Paris, all of France

[73] Assignee: ELA Medical S.A., Montrouge, France

[21] Appl. No.: 405,286

[22] Filed: Mar. 16, 1995

[30] Foreign Application Priority Data

Mar. 16, 1994 [FR] France ................. 94 3039

[51] Int. Cl.⁶ .................. A61N 1/36; A61N 1/365
[52] U.S. Cl. .................. 607/19; 607/25
[58] Field of Search .................. 607/19, 25

[56] References Cited

U.S. PATENT DOCUMENTS

| | | | |
|---|---|---|---|
| 4,428,378 | 1/1984 | Anderson et al. | 607/19 |
| 4,712,556 | 12/1987 | Baker, Jr. | 128/419 PG |
| 4,856,523 | 8/1989 | Sholder et al. | 607/17 |
| 4,892,100 | 1/1990 | Schaldach | 607/19 |
| 4,926,863 | 5/1990 | Alt | 607/19 |
| 5,040,534 | 8/1991 | Mann et al. | 607/19 |
| 5,044,365 | 9/1991 | Webb et al. | 607/19 |
| 5,143,065 | 9/1992 | Adkins et al. | 607/19 |
| 5,215,084 | 6/1993 | Schaldach | 607/19 |
| 5,249,572 | 10/1993 | Bonnet | 607/20 |
| 5,282,839 | 2/1994 | Roline et al. | 607/19 |
| 5,300,092 | 4/1994 | Schaldach | 607/19 |
| 5,303,702 | 4/1994 | Bonnet et al. | 607/20 |
| 5,312,451 | 5/1994 | Limousin et al. | 607/15 |
| 5,330,510 | 7/1994 | Legay et al. | 607/19 |
| 5,417,715 | 5/1995 | Noren et al. | 607/9 |
| 5,447,524 | 9/1995 | Alt | 607/19 |
| 5,514,162 | 5/1996 | Bornzin et al. | 607/19 |

FOREIGN PATENT DOCUMENTS

| | | | |
|---|---|---|---|
| 080348 | 11/1982 | European Pat. Off. | A61N 1/365 |
| 203027 | 2/1986 | European Pat. Off. | A61N 1/365 |
| 326629 | 2/1988 | European Pat. Off. | A61N 1/365 |
| 313881 | 10/1988 | European Pat. Off. | A61N 1/365 |
| 493220A1 | 12/1991 | European Pat. Off. | A61N 1/365 |
| WO86/07270 | 12/1986 | WIPO | A61N 1/36 |
| WO91/01157 | 2/1991 | WIPO | A61N 1/365 |

*Primary Examiner*—William E. Kamm
*Assistant Examiner*—Carl H. Layno
*Attorney, Agent, or Firm*—Orrick, Herrington & Sutcliffe, LLP

[57] ABSTRACT

Process of control of the base frequency of a cardiac pacemaker having at least one sensor monitoring a physiological parameter. Rest phases and resumption of activity phases are detected to adapt automatically the base frequency of the pacemaker to the relative periods of rest and activity of the patient. Thus, the base frequency is allowed to decrease below the normally programmed base frequency in response to actual patient rest, to encourage a low spontaneous cardiac rhythm to inhibit pacing.

48 Claims, 3 Drawing Sheets

METHOD AND APPARATUS FOR CONTROLLING THE BASE FREQUENCY OF A CARDIAC PACEMAKER

FIELD OF THE INVENTION

The invention concerns control of the base frequency of a cardiac pacemaker, more particularly, a cardiac pacemaker having at least one sensor to monitor a physiological parameter, which adjusts the base frequency on the pacemaker in response to patient activity.

The present invention also concerns a pacemaker having the function of "enslavement" of the stimulation frequency to a physiological parameter, i.e., rate responsive or metabolic demand pacemaker in which the pacing rate is controlled as a function of a monitored physiological parameter indicative of the patient's activity level and/or cardiac output requirements; but this last function can be insured by a different sensor than the sensor and physiological parameter which controls the base frequency.

BACKGROUND OF THE INVENTION

In a cardiac pacemaker, also called a cardiac pulse generator, it is usual to define a base frequency (or basic rate) at which stimulation pulses are delivered in the absence of a spontaneous cardiac rhythm. The base frequency value is typically programmed. It is understood that a base frequency in hertz or beats per minute has a corresponding time interval in seconds, usually expressed in ms. The base interval also is referred to as a basic escape interval ("EI"), which interval starts at a first cardiac event, and results in a stimulation pulse being delivered at the end of the interval unless a spontaneous cardiac event occurs before the end of the interval.

As appreciated by the inventors, during periods when the patient is at rest, a spontaneous cardiac rhythm can exist which is below the base frequency, and which is physiologically compatible with the state of the patient. A problem which exists with conventional pacemakers, however, is that the regulation of the device at the programmed base frequency will not be able to accommodate such a spontaneous rhythm below the base frequency.

Several attempts have been proposed to vary the base frequency function during periods of rest and activity of the patient.

U.S. Pat. No. 5,143,065 describes a predictable model, in which the base frequency is adjusted as a function of the time of day and cyclic physiological needs of the patient.

The document WO 86/07270 describes a function simulating the day and night variations (circadian rhythm) of the natural cardiac rhythm.

None of these documents, however, allows the adaptation of the base frequency to periods of real activity or effective rest of the patient.

SUMMARY OF THE INVENTION

It is, therefore, an object of the invention to provide a cardiac pacemaker whose programmed base frequency is automatically adapted to the physiological needs of the patient, during diurnal or nocturnal rest phases, as well as during phases of return to a non-rest or active state.

Broadly, the present invention is directed to control of the base frequency in a cardiac pacemaker having at least one sensor to monitor a physiological parameter, characterized in that rest phases and phases of resumption of activity of the patient are detected to adapt automatically the base frequency of the pacemaker to periods of rest and activity of the patient. This allows a base frequency to be applied (also called the "current base frequency") that is different than the programmed base frequency, without reprogramming the device, and allows a spontaneous cardiac rhythm to inhibit pacing during rest phases when such a spontaneous rhythm is physiologically acceptable and below the programmed base frequency. For convenience, the phase of resumption of activity is also referred to as an "active" phase.

Preferably, rest phases and active phases are determined by analysis of (1) the information signal provided by the sensor, which information is representative of patient activity as detected by the sensor (herein the "sensor activity"), and (2) the spontaneous or stimulated cardiac rhythm representative of patient activity as detected by, e.g., pacemaker circuits being inhibited from pacing or delivering stimulation pulses, or from analyzing an intracardiac electrogram or an external ECG signal, or some combination thereof (herein the "cardiac activity"). The analysis to be performed is to determine when each of the sensor activity and cardiac activity correspond to the rest conditions and/or active conditions.

In this regard, the following definitions are used. A "rest phase" is defined as when there is defined a phase or period of "sensor rest" or a phase of "cardiac rest." In a more preferred embodiment, a rest phase is defined when there are defined both a sensor rest and a cardiac rest phase simultaneously. An "active phase" is defined as when the conditions for a rest phase are not satisfied, such as when there is defined one or both of a phase of "sensor active" and a phase of "cardiac active", depending on the embodiment. A phase of "sensor rest" is defined as when, for a number p comparisons or samples, an average of the sensor information signal is below a rest level of the sensor a number r out of p times, wherein $r \leq p$, and otherwise a phase of "sensor active" is defined (i.e., when the sensor average is below the rest level of the sensor less than r out of p times). For example, and without limitation, the criteria distinguishing sensor rest from active states may be when the sensor average is below or above the sensor rest level on any 5 out of 8 consecutive comparisons.

Preferably, the sensor average is defined as an average of the last information provided by the sensor during a first programmable duration. The first programmable duration may be defined by a clock (i.e., a time interval), or by a preselected number of respiratory cycles. Preferably also, the sensor average is calculated at regular intervals whose duration corresponds to a second programmable duration, which duration also is defined by a clock, or by a number of respiratory cycles. Thus, the average may be based on a sliding window of sensor information, or successive discrete portions of sensor information, which may be contiguous or non contiguous portions. Of course, weighted averages could be used if desired.

A "cardiac rest" phase is defined as when during N cardiac cycles, the percentage of the N cardiac cycles for which the interval between two consecutive cardiac events of a similar nature is greater than the current base interval decreased by a threshold, is greater than a programmable value Y %. Stated otherwise, for a sample of N cardiac cycles, the number of cardiac cycles having an interval between two consecutive cardiac events of a similar nature (i.e., an escape interval) that is greater than x, when x equals the current base interval decreased by a threshold, is counted as a value z. If the percentage of such intervals in the sample set, namely z/N, is greater than a programmable value Y %, then the cardiac rest phase is defined. Alternatively, the cardiac rest phase may be defined as when during S cardiac cycles the interval between two consecutive cardiac events of similar nature is greater than the current base interval decreased by a threshold. This latter test is typically based on a series of consecutive cardiac cycles having a cardiac escape interval below the current base interval decreased by a threshold.

A "cardiac active" phase is defined as when during N cardiac cycles, the percentage of cardiac cycles for which the interval between two consecutive cardiac events of a similar nature is greater than the current base interval decreased by a threshold, is less than or equal to a programmable value Y %. Alternatively, the cardiac active phase may be defined as when during S cardiac cycles, the interval between two consecutive cardiac events of a similar nature is less than or equal to the current base interval decreased by a threshold.

In accordance with the invention, after each rest phase, the current base interval is preferably prolonged by an increment, which is preferably programmable, and more preferably prolonged by a programmable increment until the current base interval reaches a maximal base interval corresponding to a minimal base frequency. Further, after each active phase, the current base interval is decreased by a programmable decrement, and more preferably decreased by a programmable decrement until the current base interval reaches a minimum base interval corresponding to the programmed base frequency.

In one aspect of the invention, a condition referred to as an extrasystole "too important" is defined. This occurs when, during N cardiac cycles, the number of atrial or ventricular extrasystoles that occur is greater than a programmable value M. When an extrasystole too important condition is defined, the current base interval is decreased by a decrement. An extrasystole, as it is well known, is a premature spontaneous cardiac event. See, e.g., U.S. Pat. No. 5,271,394.

In accordance with the invention, the enslavement of the frequency of stimulation to a physiological parameter detected by the sensor remains always functional, regardless of the current base frequency. Stated otherwise, the rate responsive stimulation frequency, determined as a function of a physiological parameter indicative of patient activity and/or cardiac output requirements, remains functional independent of the current base frequency.

The invention also is directed to a rate responsive cardiac pacemaker having at least one sensor for monitoring a physiological parameter, characterized in that it detects rest and activity phases of the patient, to adapt automatically the base frequency of stimulation. Such a pacemaker includes at least one such physiological sensor, signal conditioning circuits, a state machine, and/or a microprocessor capable of operation in the above described process to adjust the base interval.

BRIEF DESCRIPTION OF THE DRAWINGS

Further features of the invention, its nature and various advantages will be apparent from the accompanying drawings and the following detailed description of the invention, in which.

DETAILED DESCRIPTION OF THE INVENTION

Figure 1:
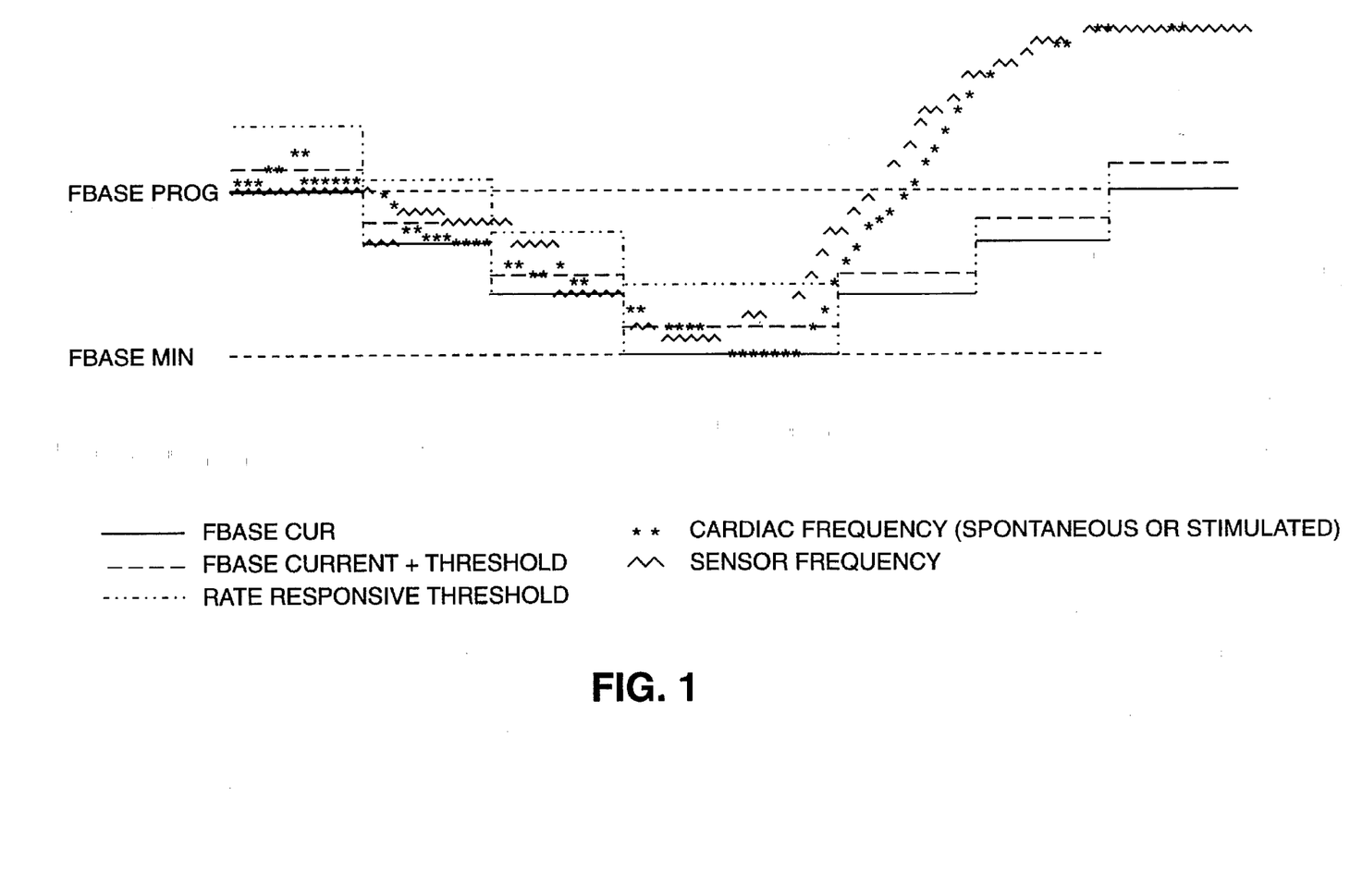
FIG. 1 is a diagram illustrating the application of a process of controlling the base frequency of the pacemaker in accordance with a preferred embodiment of the invention.

Referring to FIG. 1, a sequence of variations, by steps, of the current base frequency, FBASE CUR, is shown, relative to a programmed base frequency, FBASE PROG, and a minimal base frequency, FBASE MIN. The sequence includes, starting at the left of FIG. 1, a period where the patient is at rest. It is illustrated how the current base frequency, FBASE CUR, declines to the minimal base frequency, FBASE MIN, over time. Then, starting near the middle of FIG. 1, after the resumption of activity of the patient, which is represented by the rise of the sensor derived frequency, SENSOR FREQUENCY, illustrated by the carrots, the current base frequency, FBASE CUR, rises over time to the programmable base value, FBASE PROG, during the sustained activity. The cardiac events CARDIAC FREQUENCY, are illustrated as asterisks.

Figure 2:
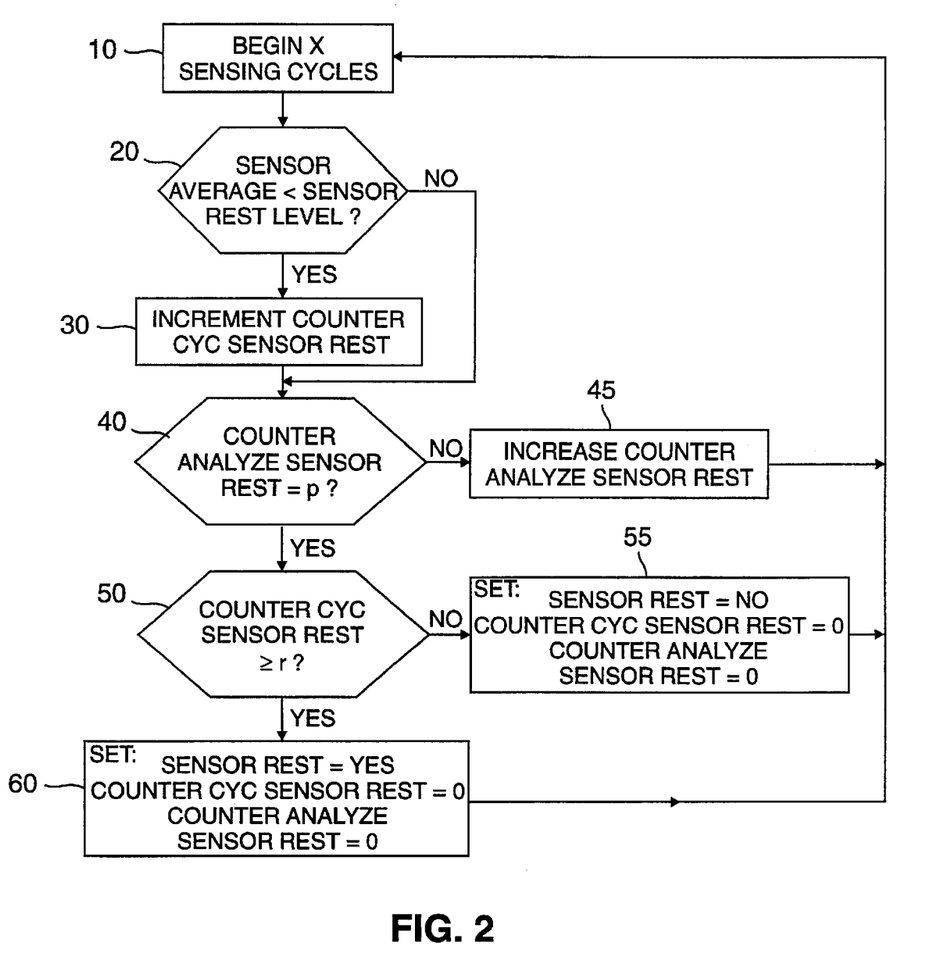
FIG. 2 is a flow chart diagram of a process for control of the sensor.

Referring to FIG. 2, a process for the control of the sensor is illustrated having for object to define, in response to the information provided by the sensor, whether there is a rest phase that is determined to be a sensor rest state.

Referring to FIG. 2, the sensor information, after having been suitably conditioned and converted for digital analysis, is preferably processed by a software controlled microprocessor as follows. At step 10, the cycle of calculating the average sensor information begins for a first predetermined duration (or a given number of respiratory cycles). At step 20, the sensor average is obtained and compared to the sensor rest level value. If the sensor average is less than the sensor rest level, then at step 30 the counter CYC SENSOR REST is incremented, and the routine passes to step 40. If the sensor average is not less than the sensor rest level, then the routine passes to step 40.

At step 40, the counter ANALYZE SENSOR REST is compared to a preselected value p. If the count value is not equal to p, then the routine increments the counter at step 45 and the routine returns to step 10 for another sensing cycle. If the ANALYZE SENSOR REST count value is equal to p, then the counter CYC SENSOR REST value is compared to a value r. If it is greater than or equal to r, then at step 60 the sensor rest state is defined as yes, and the counters CYC SENSOR REST and ANALYZE SENSOR REST are reset to zero. The routine then returns to step 10 for another sensing cycle. If the counter CYC SENSOR REST value is not greater than or equal to r, then at step 55 the sensor rest state is defined as no, and the counters CYC SENSOR REST and ANALYZE SENSOR REST are reset to zero. The routine then returns to step 10 for another sensing cycle.

Figure 3:
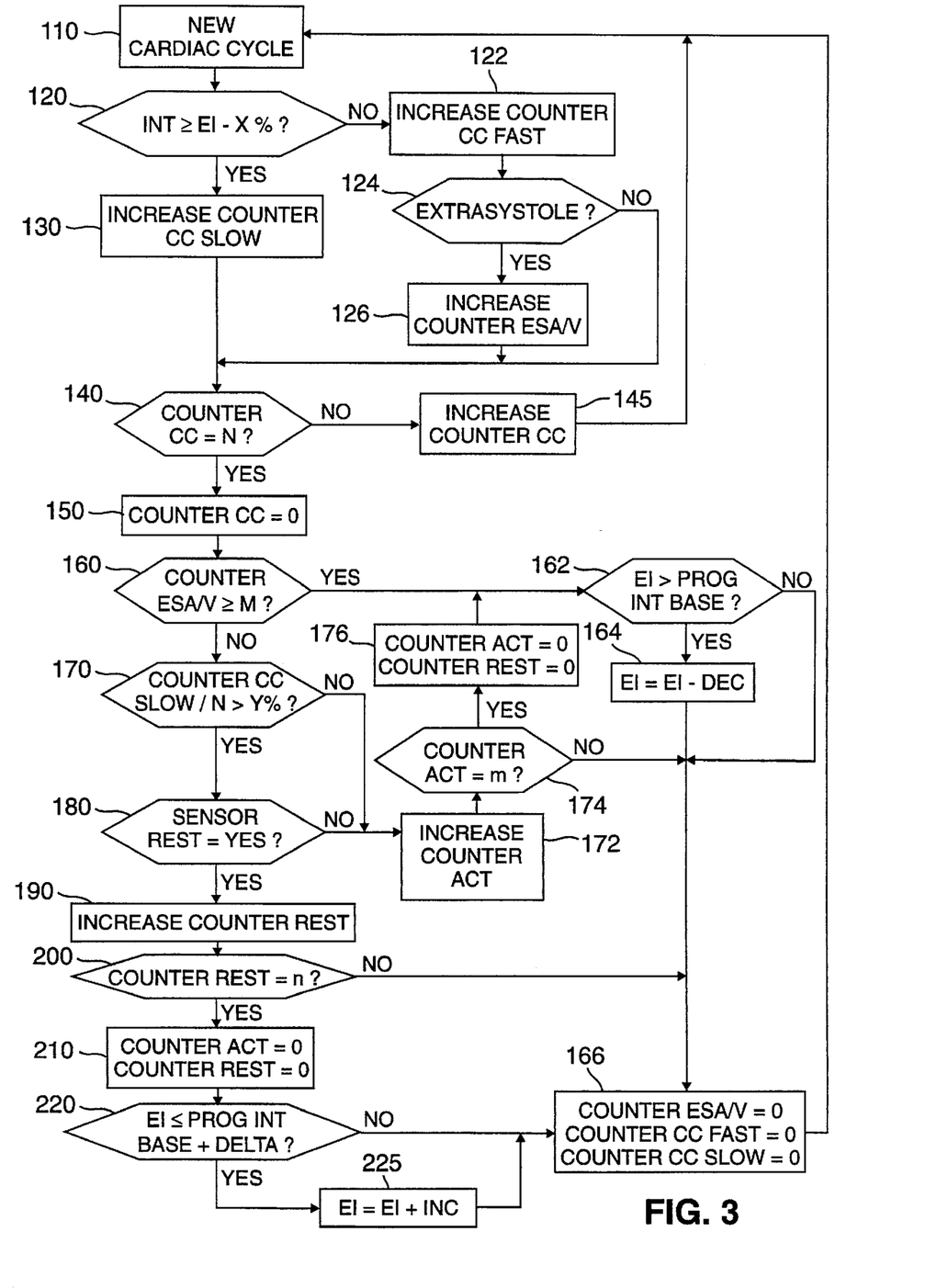
FIG. 3 is a flow chart diagram of a process for implementing the process of control of the base frequency in accordance with an embodiment of the invention.

Referring to FIG. 3, a process for the control of the pacemaker is illustrated, having for object to define, by monitoring cardiac events, if there is a rest phase that is determined to be a cardiac rest phase. When the rest state is defined both by the information provided by the sensor and by monitoring cardiac events, i.e., by the process illustrated in FIGS. 2 and 3, that is to say that there is both a state of sensor rest and a cardiac rest state, then the process of the present invention controls the decrease of the current base frequency, from the programmed base frequency, FBASE PROG, to the minimal base frequency, FBASE MIN. This decrease occurs automatically and by steps. When, during a period of rest, i.e., a defined rest phase, an activity is detected, the process of the invention controls the increase of the current base frequency from the minimal base frequency, FBASE MIN, to the programmed base frequency, FBASE PROG. This increase also occurs automatically and by steps. Thus, the invention controls the current base frequency between the programmed base frequency and a minimal base frequency, as a function of the relative periods of time that the patient is in a rest phase, and in an active phase automatically.

Referring to FIG. 3, the process for evaluating the cardiac activity together with the sensor activity information is shown. The routine starts at each cardiac cycle at step 110. At step 120, the interval INT between two consecutive cardiac events of the same kind or nature, e.g., two R waves, is compared to the current base interval EI that has been decremented by some threshold, e.g., x % of the current base interval. If the interval INT is greater than or equal to the decremented current base interval EI, then at step 130 a counter CC SLOW is incremented. The counter CC SLOW counts the number of intervals INT corresponding to a slow cardiac rhythm near the current basis frequency EI. Next, at step 140, a counter CC is compared to the number N representing the plurality of cardiac cycles being examined. If the counter CC is not equal to N, then the routine increments counter CC at step 145 and returns to step 110 for the next cardiac cycle to acquire the next interval INT. If however, the counter CC is equal to N, then at step 150 the counter CC is reset to zero, and the routine then examines the cardiac state of the patient.

In the case that the interval INT is not greater than or equal to the current base interval EI, then at step 122 a counter CC FAST is incremented. The counter CC FAST counts the number of intervals INT corresponding to a faster cardiac rhythm. Next, at step 124, the interval INT is tested to determine whether it is an extrasystole, either atrial or ventricular. This test may be performed in any conventional manner, e.g., by comparing the interval to one or more preset time periods. If it is an extrasystole, then a counter ESA/V is incremented, and the routine passes to step 140. If it is not an extrasystole, then the routine passes directly to step 140.

After resetting counter CC, the routine examines the counter ESA/V relative to a preselected or programmable value M at step 160. If the test is positive, indicating that there are too many extrasystoles, then the routine passes to step 162 where the current base interval EI is compared to the programmed base interval PROG INT BASE. If the current base interval EI is not greater than the programmed base interval PROG INT BASE, then the routine passes to step 166 wherein the counters ESA/V, CC FAST, and CC SLOW are reset to zero, and the routine then passes to step 110 to begin a new sequence of N cardiac cycles. If, however, the current base interval EI is greater than the programmed base interval PROG INT BASE, then the current base interval EI is decremented by a value DEC at step 164, and the routine then passes to step 166 to continue as described.

In the case that the counter ESA/V is less than the value M, then at step 170 the percentage of slow intervals, namely the count of counter CC SLOW divided by N, is compared to a predetermined fraction Y %. If the percentage is not greater than Y %, then a counter ACT is incremented at step 172, and the counter ACT is compared to a programmed value m. If the count of counter ACT is greater than m, then the counters ACT and REST are reset to zero at step 176, and the routine passes to step 162, where it continues in the sequence already described. If the counter ACT count is not equal to m, then the routine passes to step 166 and continues in the sequence already described.

If, however, the percentage is greater than Y %, then at step 180, the sensor state is tested to determine if it is in a sensor rest state. If it is not, then the routine passes to step 172 where the counter ACT is incremented, and continues as described. If there is a defined sensor rest state, then at step 190 the counter REST is incremented, and the counter REST value is compared to a predetermined value n at step 200. If the counter REST value is equal to n, then the routine passes to step 166 to reset the counters and continue as already described. If it is not equal to n, then at step 210 the counters ACT and REST are reset to zero and at step 220 the current base interval EI is compared to the sum of the programmed base interval PROG INT BASE and DELTA, where DELTA is a programmable value. If the current base interval EI is less than the programmed base interval plus delta, then at step 225 the current base interval EI is incremented by the amount INC and the routine passes to step 166. Otherwise, the routine passes directly to step 166.

In accordance with the present invention, the sensor rest and sensor active state of the patient is detected, for example, by a sensor of activity detecting movements of the trunk, e.g., an accelerometer, or by a sensor measuring the minute ventilation. Many such pacemaker physiological parameter sensors are known. In addition, several sensors can be foreseen, i.e., more than one sensor of different physiological parameters can be used in the same device, such as an accelerometer and an electrode/impedance system for measuring minute ventilation.

To define a state of sensor rest, an average of the last information provided by the sensor is calculated at regular intervals. These intervals are preferably programmable and correspond to, for example, 32 respiratory cycles in the case of minute ventilation. In one embodiment, the sensor average is based on the last information of the sensor corresponding to, for example, the last 128 respiratory cycles, which number is programmable. Thus, the sensor average, i.e., the average of the last information of the sensor, is for example, the average of the minute ventilation measures obtained over the last 128 respiratory cycles. This average may then be related to a corresponding stimulation frequency in a known manner. In one embodiment, the average over the last 128 cycles may be determined after the next 128 cycles, or after 64 cycles, or some other number of cycles, preferably a multiple of four cycles.

In an alternate embodiment, the sensor can monitor a physiological parameter that is not directly connected with the breathing of the patient. For example, the sensor can be of the type which measures acceleration, to follow the movement-type activity of the patient. In this case, it is preferred to base the sensor average on a duration, rather than any number of respiratory cycles.

A sensor rest state, as noted, is defined as when the sensor average is less than the rest level of the sensor, for example, for r out of p times, with $r \leq p$. The numbers r and p are desirably programmable.

The rest level of the sensor is determined as a function of the daily rhythm of the patient, for example, by the automatic calibration routine described in the document FR-A-2,671,013 and the corresponding and commonly owned U.S. Pat. No. 5,303,702, the disclosure of which is hereby incorporated herein by reference.

A sensor active state is defined when the sensor average is below the rest level of the sensor, in less than r out of p samples, with $r \leq p$.

A cardiac rest state is determined for a plurality N of cardiac cycles, wherein the number N is programmable. A cardiac cycle is defined by an interval between two consecutive cardiac events that are similar in nature, for example, the interval between two consecutive P waves (i.e., spontaneous or paced atrial events), or the interval between two consecutive R waves (i.e., spontaneous or paced ventrical events). In the framework of the present invention, the interval is usually defined as the duration between two consecutive R waves.

During the N cardiac cycles, a percentage of the N cardiac cycles is calculated, in which the interval between each two consecutive, similar cardiac events is greater than the interval of the current base decreased by a threshold. If this percentage is greater than a programmable value Y %, then a cardiac rest state is defined. If this percentage is less than or equal to this programmable value Y %, then a cardiac active state is defined.

In an alternative embodiment, it is possible to define the cardiac rest state when, during S cardiac cycles, the interval between two consecutive cardiac events of a similar nature is greater than the interval of the current base interval decreased by a threshold. The cardiac active state is then defined when, during the S cardiac cycles, at least one of the intervals is less than or equal to the interval of the current base interval decreased by a threshold.

During the N cardiac cycles, the pacemaker detects and counts the number of atrial or ventricular extrasystoles, which number is memorized in the counter ESA/V (FIG. 3). If the number of extrasystoles is greater than a programmable value M, then an extrasystole "too important" condition is defined.

The process of increasing or decreasing the current base frequency in accordance with the present invention is generally described, with reference to FIG. 3, in the following manner:

If, during a programmable number n (controlled by counter REST) of periods of N cardiac cycles, a sensor rest and a cardiac rest are simultaneously defined, then the current base interval is prolonged by a programmable increment, until the current base interval reaches the interval of the minimal base frequency. This minimal base frequency is preferably equal to the programmed base frequency decreased by a programmable frequency delta.

If during a programmable number m (controlled by counter ACT) of periods of N cardiac cycles, a sensor active state or a cardiac active state is defined, then the current base interval is decreased by a programmable decrement, until the current base interval reaches an interval corresponding to the programmed base frequency.

If during a period of N cardiac cycles, a extrasystole too important is defined, then the current base interval is decreased by a programmable decrement, until the current base interval reaches the interval of the programmed base frequency.

The cardiac pacemaker used is, for example, of the dual chamber rate responsive type. Such pacemakers are known, e.g., the model CHORUS RM cardiac pacemaker available from ELA Medical SA, Montrouge, France, which can be adapted to perform the present invention by a person of ordinary skill in the art. Other types of rate responsive pacemakers also may be used, including single chamber devices such as the OPUS-G pacemaker, also available from ELA Medical SA.

Such pacemakers typically include hardware circuits for sensing cardiac activity, and circuits for detecting a signal representative of the physiological parameter being monitored, signal conditioning and filtering circuits, and a processing unit, such as a software controlled microprocessor, for operating on the acquired cardiac activity signal and sensor activity signal to identify the various cardiac and sensor states and for adjusting the base frequency in response to these states in accordance with the present invention. Suitable designs for rate adaptive pacemakers that could be modified for use with the present invention also are described in copending and commonly assigned U.S. patent application Ser. Nos. 08/346,027, filed Nov. 29, 1994, and commonly assigned U.S. Pat. Nos. 5,330,510, 5,303,702, and 5,249,572, the disclosures of which are hereby incorporated herein by reference in their entirety.

When conditions of rest are present, that is to say when the pacemaker has detected a rest phase, the current base interval is increased by a programmable duration, typically of 8 to 16 ms, until the current base interval reaches the maximal base interval corresponding to the minimal base frequency.

The patient can return to a phase of activity (an active phase) after a period of rest, that is to say while the current base frequency is less than the programmed base frequency. When the pacemaker detects such an active phase, the current base interval is decreased by a programmable duration, typically of 8 to 16 ms, until the current base interval reaches the programmed base interval corresponding to the programmed base frequency.

The enslavement function of the rate adaptive pacemaker remains always functional, regardless of the current base frequency, and does not modify the functioning of the adjustment of the current base frequency/interval. In a device having two or more different sensors, only one sensor may be used to control the base interval.

A cycle with an atrial or ventricular extrasystole does not modify the counting under way of cycles of rest.

Suitable programmable parameters are, for example, found among the following, with their tolerance values and an indication of a nominal value:

| Parameter | Values | Nominal |
|---|---|---|
| Interval of sensor average | 16–128 | 32 respiratory cycles |
| No. of cycles of the sensor average | 32–256 | 128 cyc. |
| Sensor rest phase r of p (r ≦ p) | 1–10 | 1 |
| Cardiac rest phase or resumption of activity (Y %) | 50–100% | 87.75% |
| Threshold | 6.25–50% | 25% |
| No. of cardiac rest cycles (N) | 10–100 | 32 card. |
| No. of cardiac cycles (S) | 10–1024 | 50 |
| Max no. of extrasystoles during rest (M) | 0–50 | 5 |
| Delta of base frequency | 0–45 | 20 bpm |
| Base frequency deceleration (n) | 1–10 | 3 |
| Base frequency acceleration (m) | 1–10 | 1 |

The process of control of the current base frequency according to the preset invention presents several advantages.

First, it allows the expression of the spontaneous cardiac rhythm below the programmed base frequency, which, for the heart, is preferable to a stimulated rhythm. Second, and by way of consequence, the duration of service, i.e., the battery life, of the pacemaker is lengthened by the reduced number of stimulation pulses.

Thus, the process of control according to the invention allows to adapt automatically the current base frequency to periods of activity and rest of the patient.

The description that precedes relates to a particular mode of realization of the invention. Variants can be anticipated without departing from the framework of the invention. For example, and without limitation, duration of observation mentioned in the description can be replaced by sliding or weighted averages, notably for the rest phase. One skilled in the art will appreciate that the present invention can be practiced by other than the described embodiments which are presented for purposes of illustration and not of limitation.

We claim:

1. A process for controlling a base frequency of a cardiac pacemaker having a sensor monitoring a physiological parameter and circuits for monitoring stimulated and spontaneous cardiac events, the base frequency having a corresponding base interval, comprising the steps of:

(a) providing an initial programmed base frequency;
   (b) monitoring an activity level of a patient;
   (c) determining whether the patient activity level corresponds to one of a rest phase and an active phase; and
   (d) adjusting the base frequency and corresponding base interval as a function of the determined rest phase to control the base frequency wherein the adjusted base frequency is variable relative to the initial programmed base frequency.

2. The process of claim 1, further comprising the step of controlling the pacemaker to have a stimulation frequency that is a function of the sensed physiological parameter independent of the current base interval.

3. The process of claim 1 wherein step (b) further comprises:

(i) monitoring a physiological parameter of a patient indicative of the patient's level of activity;
   (ii) analyzing the monitored parameter and identifying therefrom a sensor rest state corresponding to a patient activity level being in a rest state; and
   (iii) monitoring patient cardiac activity including spontaneous and stimulated cardiac events and identifying therefrom a cardiac rest state corresponding to the patient cardiac activity level being in a rest state.

4. The process of claim 3 wherein step (c) further comprises determining that a rest phase exists by determining that one of a cardiac rest state and a sensor rest state exists.

5. The process of claim 3 wherein step (c) further comprises determining that a rest phase exists by determining that a cardiac rest state and a sensor rest state exist simultaneously.

6. The process of claim 5 wherein step (b)(iii) further comprises:

selecting sensed cardiac events for a plurality of cardiac cycles, identifying successive cardiac events that are similar in nature, and determining an interval between each said identified two similar successive cardiac events;
   determining a percentage of the plurality of cardiac cycles for which the determined interval between said two identified consecutive similar cardiac events is greater than the base interval decreased by a threshold; and
   determining that the cardiac activity level is in a rest state in response to the determined percentage being greater than a first value.

7. The process of claim 5 wherein step (b) (iii) further comprises:

selecting sensed cardiac events for a plurality of cardiac cycles, identifying successive cardiac events that are similar in nature, and determining an interval between each said identified two similar successive cardiac events; and determining that the cardiac activity level is in a rest state in response to the determined interval between said two identified consecutive similar cardiac events being greater than the base interval decreased by a threshold.

8. The process of claim 5 wherein step (d) further comprises the steps of determining the end of a rest phase, and, in response thereto, increasing the base interval by an increment.

9. The process of claim 8 wherein increasing the base interval by an increment further comprises determining whether or not the base interval has reached a maximum interval limit corresponding to a minimal base frequency, and if it has, not further increasing the base interval.

10. The process of claim 3 wherein step (b)ii further comprises averaging monitored physiological parameters, determining an average value of the monitored physiological parameter for each of p samples and determining that the average is less than a predetermined sensor rest level for r out of p samples, wherein r≦p.

11. The process of claim 10 wherein determining the average value further comprises providing a first duration and providing an average of the last information provided by the sensor during said first duration.

12. The process of claim 11 wherein monitoring the physiological parameter further comprises monitoring respiration, the method further comprising determining a respiratory cycle and providing said first duration as one of a first time interval and a first number of respiratory cycles.

13. The process of claim 12 wherein determining the average further comprises periodically calculating the average at regular intervals corresponding to a second duration, the second duration being one of a second time interval and a second number of respiratory cycles.

14. The process of claim 3 further comprising step (e) determining that an active phase exists by determining that a cardiac rest state and a sensor rest state do not exist simultaneously; wherein step (d) further comprises adjusting the base interval as a function of the determined rest and active phases.

15. The process of claim 14 wherein step (e) further comprises:

selecting sensed cardiac events for a plurality of cardiac cycles, identifying successive cardiac events that are similar in nature, and determining an interval between each said two identified similar successive cardiac events;
   determining a percentage of the plurality of cardiac cycles for which the determined interval between said two identified consecutive similar cardiac events is less than or equal to the base interval decreased by a threshold; and
   defining said cardiac active phase to exist in response to the determined percentage being less than or equal to a first value.

16. The process of claim 14 wherein step (e) further comprises:

selecting sensed cardiac events for a plurality of cardiac cycles, identifying successive cardiac events that are similar in nature, and determining an interval between each said two identified similar successive cardiac events; and
   defining said cardiac active phase to exist in response to the determined interval between said two identified consecutive similar cardiac events being less than or equal to the base interval decreased by a threshold.

17. The process of claim 14 wherein step (d) further comprises the steps of determining the end of an active phase, and in response thereto decrementing the base interval by a decrement.

18. The process of claim 17 wherein decrementing the base interval by the decrement further comprises determining whether the base interval has reached a minimum interval limit corresponding to a second programmed base frequency, and if it has, not further decreasing the base interval.

19. The process of claim 14 further comprising:
selecting sensed cardiac events for a plurality of cardiac cycles, wherein the sensed cardiac events include at least one of atrial and ventricular extrasystole cardiac events;
counting the number of atrial and ventricular extrasystole cardiac events in said plurality of cardiac cycles; and
defining an extrasystole too important condition in response to the number of atrial and ventricular extrasystoles being greater than a first number.

20. The process of claim 19 wherein step (d) further comprises the step of decreasing the base interval in response to a defined extrasystole too important condition.

21. The process of claim 14 wherein step (e) further comprises determining an average value of the monitored parameter for each of p samples, and determining that the average is less than a predetermined sensor rest level for less than r out of p samples, wherein $r \leq p$.

22. The process of claim 21 wherein determining the average value further comprises providing a first duration and providing an average of the last information provided by the sensor during said first duration.

23. The process of claim 22 wherein monitoring the physiological parameter further comprises monitoring respiration, the method further comprising determining a respiratory cycle and providing a duration as one of a first time duration and a first number of respiratory cycles.

24. The process of claim 23 wherein determining the average further comprises periodically calculating the average at regular intervals corresponding to a second duration, the second duration being one of a second time interval and a second number of respiratory cycles.

25. An apparatus for controlling a base frequency of a cardiac pacemaker, the base frequency having a corresponding base interval, comprising:
an initial programmed base frequency;
first means for determining an activity level of the patient and determining whether the patient activity level corresponds to one of a rest phase and an active phase; and
means for automatically adjusting the base interval as a function of a determined rest phase wherein the adjusted base interval varies relative to the initial programmed base frequency.

26. The apparatus of claim 25 wherein said first determining means further comprises:
a sensor having an output signal corresponding to a physiological parameter of a patient indicative of the patient's level of activity;
means for analyzing the sensor output signal and identifying therefrom a sensor rest state corresponding to a patient activity level in a rest state; and
means for processing the detected cardiac events and identifying therefrom a cardiac rest state corresponding to a patient cardiac activity level in a rest state.

27. The apparatus of claim 26 wherein the first determining means further comprises a second means for determining that a rest phase exists in response to the existence of one of an identified sensor rest state and an identified cardiac rest state.

28. The apparatus of claim 26 wherein the first determining means further comprises a second means for determining that a rest phase exists in response to a cardiac rest state and a sensor rest state existing simultaneously.

29. The apparatus of claim 26 wherein said processing means further comprises means for selecting the sensed cardiac events for a plurality of cardiac cycles, means for identifying two successive cardiac events that are similar in nature, means for determining an interval between each said identified two similar successive cardiac events, and means for determining a percentage of the plurality of cardiac cycles for which the determined interval between said two identified consecutive similar cardiac events is greater than the base interval decreased by a threshold, and means for determining that the cardiac activity level is in a rest state in response to the determined percentage being less than or equal to a first value.

30. The apparatus of claim 26 wherein said processing means further comprises means for selecting the sensed cardiac events for a plurality of cardiac cycles, means for identifying two successive cardiac events that are similar in nature, means for determining an interval between each said identified two similar successive cardiac events, and means for determining a cardiac activity level that is in a rest state in response to the determined interval between said two identified consecutive similar cardiac events being greater than the base interval decreased by a threshold for said plurality of cardiac cycles.

31. The apparatus of claim 26, further comprising a pacemaker having said base interval and means for detecting cardiac events and producing a stimulation frequency that is a function of the sensed physiological parameter independent of the automatically adjusted base interval.

32. The apparatus of claim 26 wherein said adjusting means further comprises means for determining an end of a rest phase, and in response thereto increasing the base interval by an increment.

33. The apparatus of claim 32 wherein the adjusting means further comprises means for not increasing the base interval above a maximum interval limit corresponding to a minimal base frequency.

34. The apparatus of claim 26 wherein said analyzing means further comprises means for determining an average value of the sensor output signal for each of a number p of samples, and means for determining that a sensor rest state exists in response to said average value being less than a predetermined sensor rest level during a number r of the p samples, wherein $r \leq p$.

35. The apparatus of claim 34 further comprising a first duration wherein said average comprises an average of the last information provided by the sensor during said first duration.

36. The apparatus of claim 35 wherein the monitored parameter comprises respiration, the analyzing means further comprises means for determining a respiratory cycle, and said first duration comprises one of a first time interval and a first number of respiratory cycles.

37. The apparatus of claim 36 wherein said analyzing means further comprises means for calculating said average value at regular intervals having a second duration, the second duration being one of a second time interval and a second number of respiratory cycles.

38. The apparatus of claim 26 further comprising second means for determining that an active phase exists in response to a cardiac rest state and a sensor rest state not existing simultaneously; and wherein said adjusting means function further comprises a function of said determined rest and active phases of the patient.

39. The apparatus of claim 38 wherein said processing means further comprises means for selecting the sensed cardiac events for a plurality of cardiac cycles, means for identifying two successive cardiac events that are similar in nature, means for determining an interval between each said identified two similar successive cardiac events, and means for determining a percentage of the plurality of cardiac cycles for which the determined interval between said two identified consecutive similar cardiac events is greater than the base interval decreased by a first threshold, and means for determining a cardiac active phase to exist in response to the determined percentage being greater than a first value.

40. The apparatus of claim 38 further comprising:

third means for determining whether a sensed cardiac event is one of an atrial extrasystole and a ventricular extrasystole;

means for counting the number of determined extrasystoles in a plurality of cardiac cycles; and means for defining an extrasystole too important condition in response to the number of atrial and ventricular extrasystoles being greater than a first number.

41. The apparatus of claim 38 wherein said processing means further comprises means for selecting the sensed cardiac events for a plurality of cardiac cycles, means for identifying successive cardiac events that are similar in nature, means for determining an interval between each said identified two similar successive cardiac events, and means for determining a cardiac activity level that is in an active state in response to the determined interval between said two identified consecutive similar cardiac events being less than or equal to the base interval decreased by a threshold for said plurality of cardiac cycles.

42. The apparatus of claim 38 wherein said adjusting means further comprises means for determining an end of an activity phase, and in response thereto, further comprises means for decrementing the base interval by a decrement.

43. The apparatus of claim 42 wherein the adjusting means further comprising means for not decrementing the base interval below a minimum interval limit corresponding to a second programmed base frequency.

44. The apparatus of claim 43 wherein the adjusting means further comprises means for decreasing the base interval in response to a defined extrasystole too important condition.

45. The apparatus of claim 38 wherein said analyzing means further comprises means for determining an average value of the sensor output signal for each of a number p of samples and means for determining that a sensor active state exists in response to said average value being less than a predetermined sensor rest level during a number r of the p samples of events, wherein $r \leq p$.

46. The apparatus of claim 45 further comprising a first duration wherein said average value comprises an average of the last information provided by the sensor during said first duration.

47. The apparatus of claim 46 wherein the monitored parameter comprises respiration, the analyzing means further comprises means for determining a respiratory cycle, and said first duration comprises one of a first time interval and a first number of respiratory cycles.

48. The apparatus of claim 47 wherein said analyzing means further comprises means for determining said average value at regular intervals having a second duration, the second duration being one of a second time interval and a second number of respiratory cycles.

* * * * *